United States Patent [19]
Ramsay et al.

[11] 3,995,164
[45] Nov. 30, 1976

[54] METHOD AND APPARATUS FOR THE DETECTION OF FOREIGN MATERIAL IN FOOD SUBSTANCES

[75] Inventors: Joseph D. Ramsay, Punta Gorda, Fla.; Gabriel Del Rossi, Woodbury, N.J.

[73] Assignee: Campbell Soup Company, Camden, N.J.

[22] Filed: Dec. 30, 1974

[21] Appl. No.: 537,117

[52] U.S. Cl. .............................. 250/510; 250/402
[51] Int. Cl.² .............................................. G21F 3/02
[58] Field of Search .......... 250/358, 359, 360, 510, 250/563, 439, 451, 456, 490, 491, 503, 505, 402; 209/111.5

[56] References Cited
UNITED STATES PATENTS

| | | |
|---|---|---|
| 3,136,892 | 6/1964 | Willett et al. ...................... 250/360 |
| 3,715,587 | 2/1973 | Burkhalter et al. ................ 250/510 |
| 3,768,645 | 10/1973 | Conway et al. .................... 250/359 |
| 3,774,041 | 11/1973 | Kaneko et al. ..................... 250/563 |
| 3,843,890 | 10/1974 | Anthony, Jr. et al. ............. 250/563 |
| 3,881,110 | 4/1975 | Hounsfield et al. ................ 250/360 |

*Primary Examiner*—David C. Nelms
*Attorney, Agent, or Firm*—Howson and Howson

[57] ABSTRACT

Foreign material in a food substance is detected by placing it in a container filled with water to a level above the top of the food substance and moving the container through an X-raying chamber, the transmitted and detected X-rays being converted to electrical signal form. The signals are thresholded and then differentiated to obtain signals indicative of the edges of the foreign material while minimizing spurious signals due to voids or bubbles in the water or to edges of the container. Preferably the oppositely-directed differentiated pulses produced at the opposite edges of foreign material are both used to indicate presence of the foreign material.

11 Claims, 14 Drawing Figures

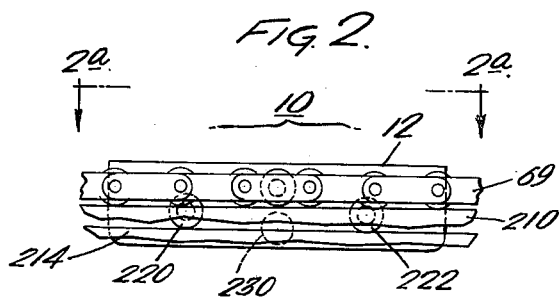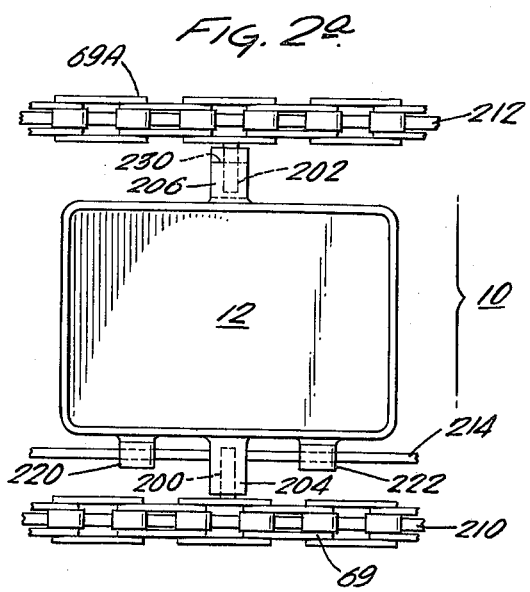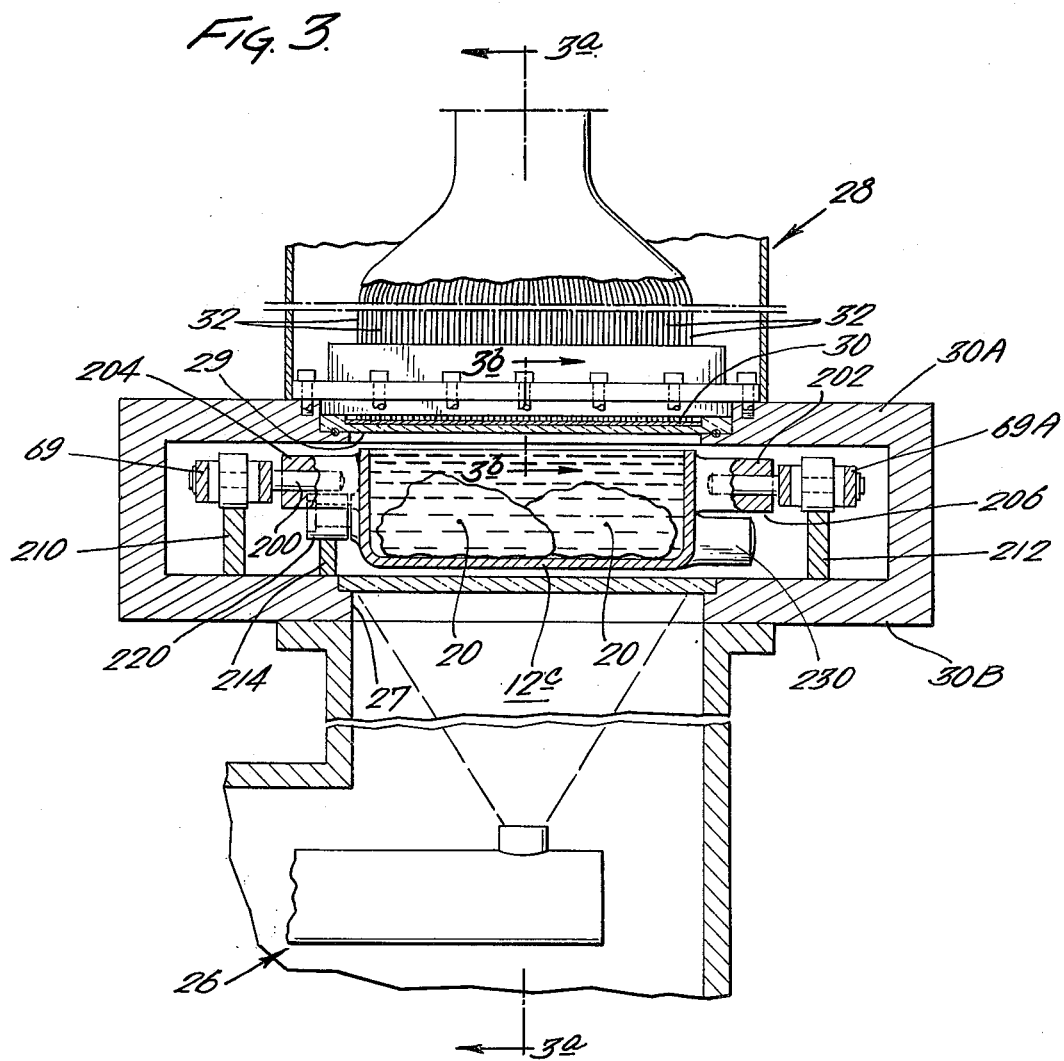

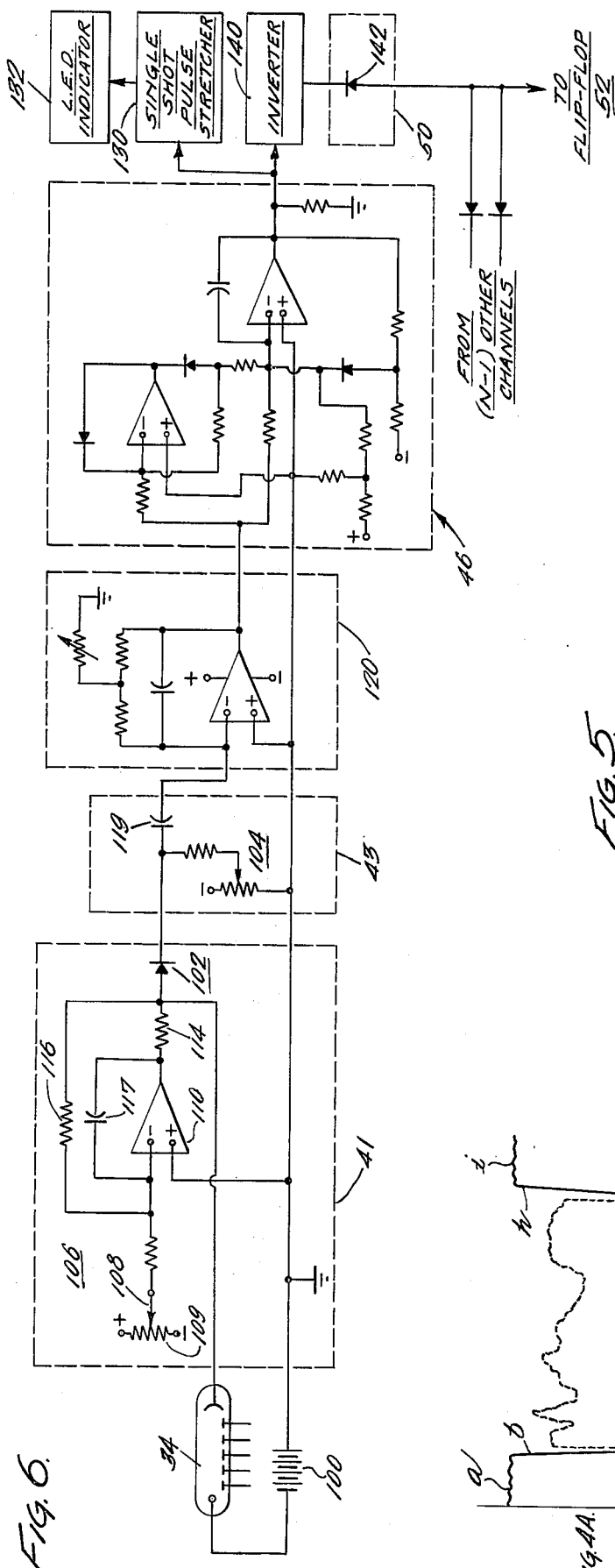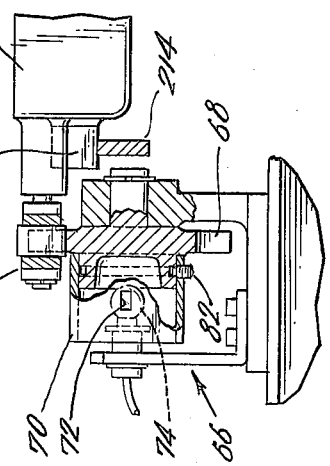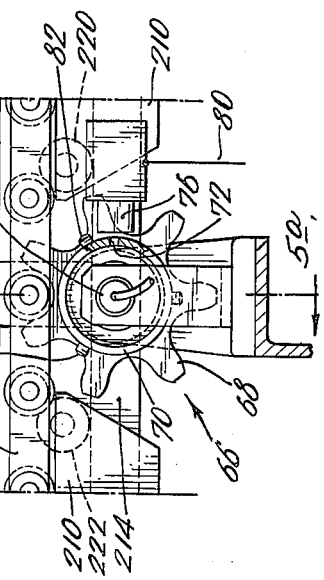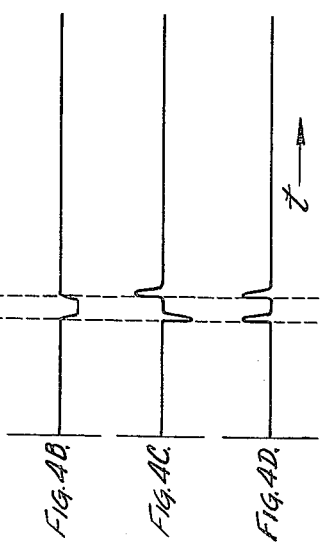

METHOD AND APPARATUS FOR THE DETECTION OF FOREIGN MATERIAL IN FOOD SUBSTANCES

BACKGROUND OF THE INVENTION

This invention relates to methods and apparatus for the detection of foreign materials in food substances, especially the detection of bones in meat, and will be particularly described with respect to the detection of chicken bones in chicken meat.

There are many known situations in which foreign material may be present in food substances, and should be detected either so it can be removed or so that the food substance containing it may be rejected or discarded. One example of such application occurs when it is desired to provide food consisting of animal meat, free of bones, under circumstances where bones unavoidably and inadvertently may occasionally be present. A specific example with respect to which the invention will be particularly described hereinafter occurs in the preparation of chicken meat for use in making chicken soup. The chicken meat is originally processed in a manner intended to remove all of the bones or bone fragments, but some always remain and if permitted to become a part of the soup present a possibility of discomfort or even harm to a consumer of the soup.

Many systems have been proposed and utilized in the past for the detection of foreign material in food substances, where it will be understood that the term "foreign material" may include material indigenous to the food substance but no longer desired therein, such as seeds, pits or bones. These prior systems include those involving transmission of various types of radiation through the food substance so as to deduce, from the intensity of the radiations transmitted to the food substance, whether or not foreign matter is present. X-rays have been proposed for this purpose, the basic operation being somewhat similar to the X-raying of human patients to detect the condition of bone or the presence of "foreign matter" in the human body. Where the foreign body to be detected has an X-ray absorption much different than that of the food substance, and where detection is to be visual by a human observer, such techniques may have a reasonable probability of success, since the image of the X-rays on a phosphorescent plate will then typically reveal discernible differences in image brightness between the region corresponding to the foreign material and immediately surrounding material; even in such systems, when the X-ray absorption coefficient of the foreign material is not very different from that of the surrounding material and/or the thickness of the foreign material is not great, detection of the foreign material can become difficult, and in the limit, impossible. Thus if the foreign material is quite thin and has an X-ray absorption coefficient only moderately different from the surrounding material, the difference in the X-ray intensity transmitted through it may not be discernibly different from the intensity of X-rays transmitted through the surrounding material.

Where the foregoing sensing of the transmitted X-rays is to be done automatically rather than visually, and an output signal reliably indicative of the presence of the foreign material is to be produced automatically, the problems of accurate and reliable detection increase. One source of such problems is that the specimen of food substance may in general have a randomly-variable thickness in the direction traversed by the X-rays. An example of this occurs with random specimens of chicken meat which are to be examined for the presence of chicken bone. Because of these random variations in thickness, the intensities of the transmitted X-rays will in general vary markedly at different points in the specimen even though no bone is present. These variations may readily be nearly as great as, or even greater than, the variations produced by bone, particularly small fragments of bone, and thus may mask the bone and prevent its reliable detection. Even if this problem due to variable meat thickness is overcome, it is still desirable to obtain the greatest possible sensitivity of detection with the smallest possible number of false indications of foreign material.

It is therefore an object of the invention to provide a new and useful method and apparatus for the detection of foreign material in a food substance.

It is also an object to provide such method and apparatus which automatically, and with a high degree of reliability, produce output signals in response to the presence of such foreign material.

Another object is to provide such method and apparatus which are capable of satisfactory operation even though the food substance is of randomly-variable thickness, and even though the extent of X-ray absorption by the foreign material is relatively small.

A further object is to provide such method and apparatus which are adapted for use in detecting foreign material in a food substance as it moves along a conveyor.

A further object is to provide such method and apparatus which are especially adapted for the detection of bone in meat, for example chicken bone in chicken meat.

SUMMARY OF THE INVENTION

These and other objects and features of the invention are realized by the provision of a method and apparatus employing at least one, and preferably all, of the following features.

Prior to exposing the food substance to X-rays, a flowable material having substantially the same coefficient of X-ray absorption as the food substance is placed about the food substance to form substantially parallel opposite surfaces for the combination of the food substance and the flowable material; the X-rays utilized to detect the presence of the foreign material are then directed along a path extending through both of these parallel opposite surfaces. In a preferred form, irregular specimens of chicken meat are placed in a flat-bottomed bucket and the bucket filled to the top with water, the X-rays then being directed to pass in series through the bottom surface of the bucket and the top surface of the water. Since the X-ray absorption coefficient of the flowable material, e.g. water, is much closer to that of the food substance than is air, in the absence of bone the intensity of the X-rays transmitted through the combination of food substances and flowable material will remain much more nearly constant than without the flowable material, so that any further decreases in transmitted X-ray intensity due to the presence of foreign material, such as bone, are much more readily and reliably detected.

Preferably the food substance is scanned by passing it continuously between an X-ray source and a plurality of elemental X-ray detectors extending across the path traversed by the food substance and opposite the X-ray source, each detector responding to X-rays transmitted through only a small portion of the food substance so that the presence or absence of the foreign material between X-ray source and detector will produce a large percentage change in the intensity of X-rays reaching that detector.

According to another preferred feature of the invention, the changes in transmitted X-ray intensity produced by both leading and trailing edges of a body of foreign material, such as a bone, are detected and both are used as an indication of the presence of the foreign material. Thus in a preferred form, an electrical signal generated by the scanning of the food substance with the X-rays is differentiated to produce a pulse at the leading edge and a pulse at the trailing edge of any bone or other foreign material, and if either such pulse is of substantial amplitude it is used to produce an output indication of the presence of foreign material. Preferably this is accomplished by unipolarizing the normally bi-polar differentiated signal, so that the pulses corresponding to the leading and lagging edges of the foreign material extend in the same direction, and any such unipolarized pulse extending above a predetermined level is used as an indication of the presence of foreign material.

As a further preferred feature of the invention, levels of the electrical signals from the X-ray detectors corresponding to transmitted X-ray intensities at least as great as those produced in the absence of bone are eliminated prior to differentiation, as by a suitable thresholding device, so that substantially the only signals supplied to the differentiating device are bone-representing signals. This prevents the generation of spurious bone-representing signals due to voids or bubbles in the flowable material surrounding the food product, which otherwise, when scanned by the X-ray system, would produce pulse signals at either the leading or trailing edge of the void or both, and which signals could produce spurious indications of the presence of foreign material.

In a preferred form of the invention, a series of flat-bottomed containers of identical form are each filled to their tops so as to completely cover the food specimen, such as chicken meat, with a liquid such as water, with the result that the threshold level beyond which signals will be taken as representing the presence of bone is very nearly the same for successive containers and specimens. As a result, this threshold level can be set to a relatively low level which permits recognition of even small amounts of foreign material, without producing substantial false output indications.

The preferred system utilizes not only the flowable material covering the food substance, but also the arrangement for moving the combination through an X-ray scanning arrangement to produce electrical signals, the differentiation of such signals only after signal levels at least as great as those corresponding to the absence of foreign material are eliminated, and the subsequent unipolarization of the differentiated signal to produce a pair of pulses of the same polarity for each fragment or body of foreign material, either of which pulses may operate an output circuit to produce an indication of the presence of the foreign matter.

BRIEF DESCRIPTION OF FIGURES

These and other objects and features of the invention will be more readily understood from a consideration of the following detailed description, taken in connection with the accompanying drawings in which:

FIG. 2 is a side elevational view showing one of the meat containers of FIG. 1 and portions of the apparatus for supporting and moving it;

FIG. 2a is a top view of the apparatus of FIG. 2 as viewed along the lines 2a—2a;

FIG. 3 is a transverse sectional view, partly in full, of the X-raying station in the system of FIG. 1;

FIG. 3a is a longitudinal sectional view of the apparatus of FIG. 3, taken along lines 3a—3a;

FIGS. 4A, 4B, 4C and 4D are graphical representations to a common time scale, showing idealized signal waveforms at various points in the system of FIG. 1;

FIG. 5 is a side view of a suitable form for the conveyor position monitor of FIG. 1;

FIG. 5a is a sectional view taken along lines 5a—5a of FIG. 5; and

FIG. 6 is an electrical schematic diagram of one typical channel in the electronic portion of the system of FIG. 1, in one of its preferred forms.

DETAILED DESCRIPTION OF SPECIFIC EMBODIMENTS

Figure 1:
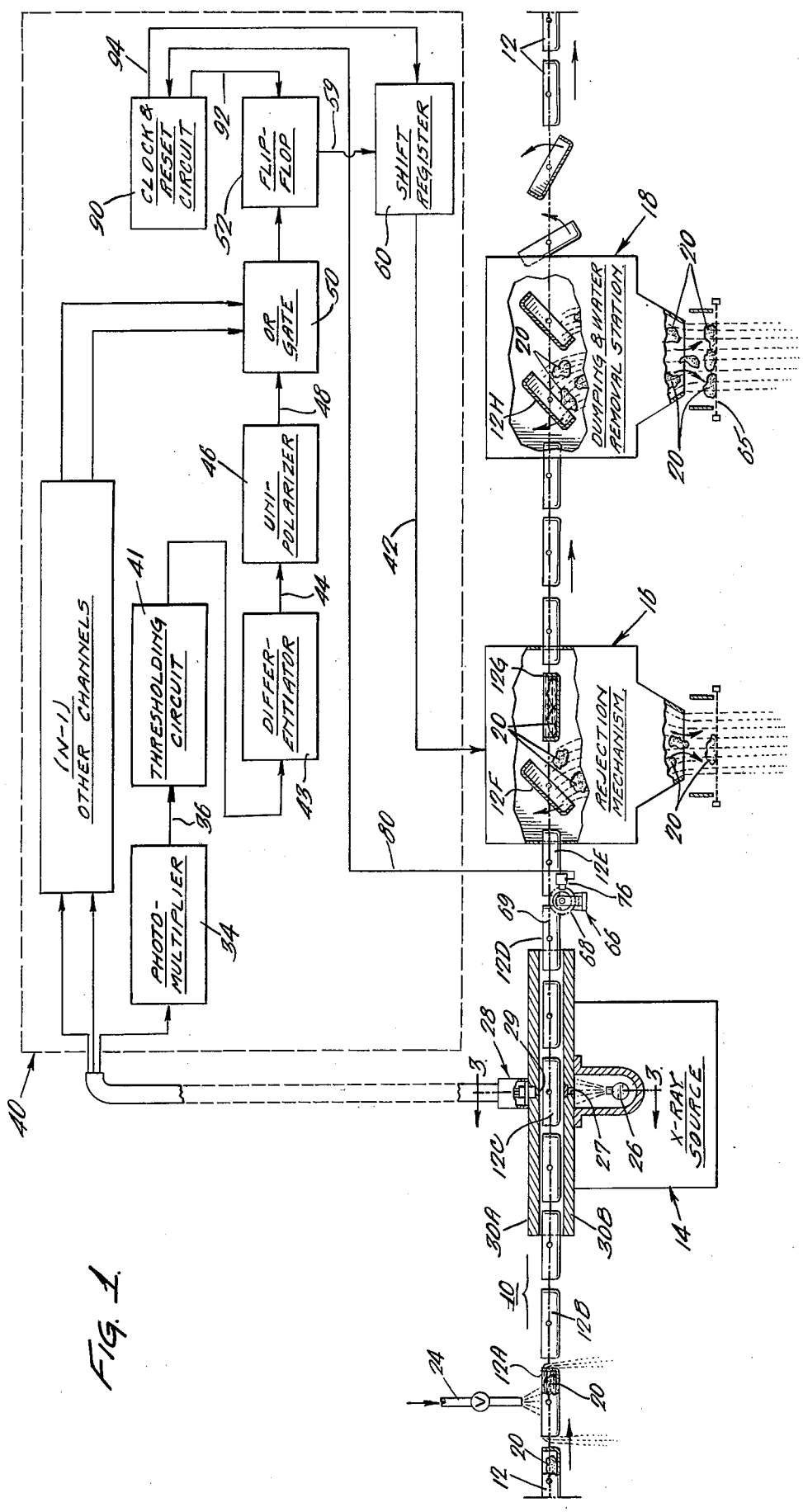
FIG. 1 is a diagram, largely schematic, of a system embodying the invention as it may be utilized to detect bone in chicken meat automatically, and to reject chicken meat specimens thus found to contain bone.

Referring now to the embodiment of the invention shown in the figures by way of example only, there is shown a conveyor arrangement 10 for carrying a succession of equally-spaced chicken meat containers such as 12, 12A, 12B, 12C, 12D, 12E, 12F, 12G and 12H through an X-ray scanning station 14 to a rejection mechanism 16 and thence through a dumping and water removal station 18 where the chicken meat 20 may be automatically dumped onto a receiver of meat to be used in making chicken soup. The chicken meat specimens are assumed to have been placed in their respective containers prior to their reaching the left-hand end of the conveyor arrangement 10 in FIG. 1, and may consist of randomly-shaped pieces of chicken meat from which all of the bone is supposed to have been removed, but in which some bones or bone fragments are nevertheless occasionally present. The top of the meat specimen is in each case located below the top of its respective container.

A water filler 24, such as a continuously running spigot, is provided above the path of the containers on the conveyor prior to the X-ray station, and delivers water into the containers such as 12A at a rate sufficient to fill each of them to overflowing as it passes beneath the spigot, so that the containers are filled to their tops when they reach the position of container 12B.

Figure 3A:
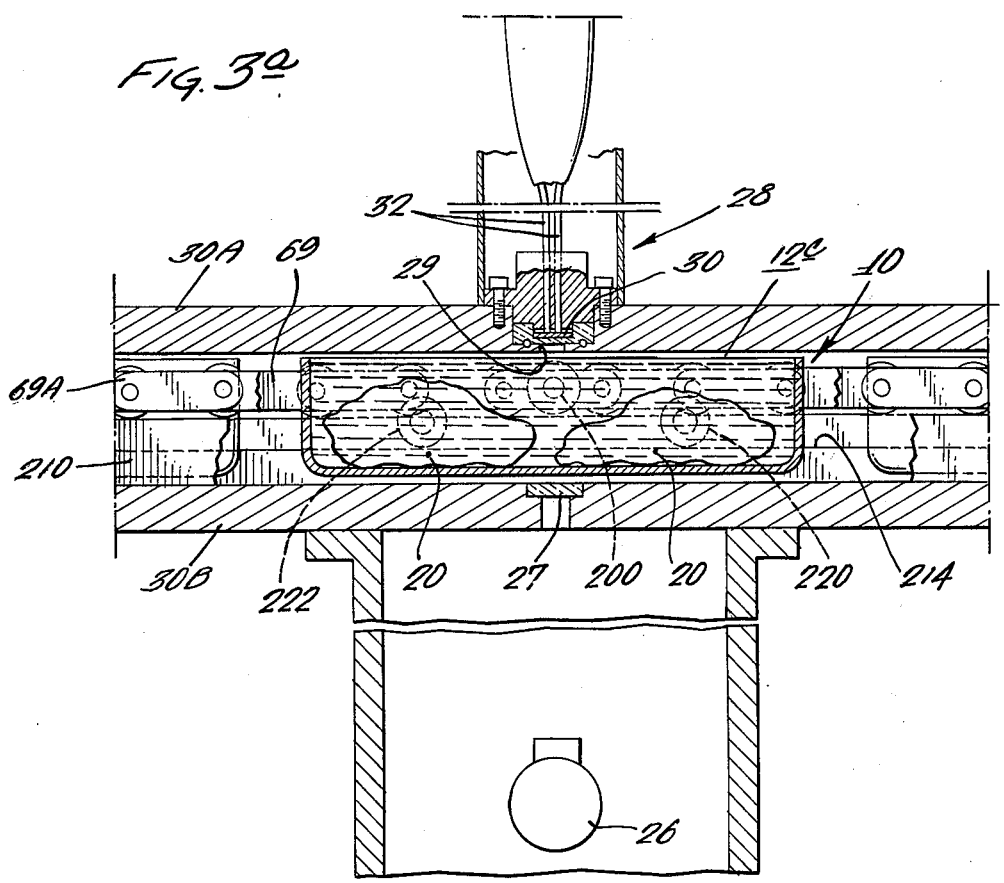
Figure 3B:
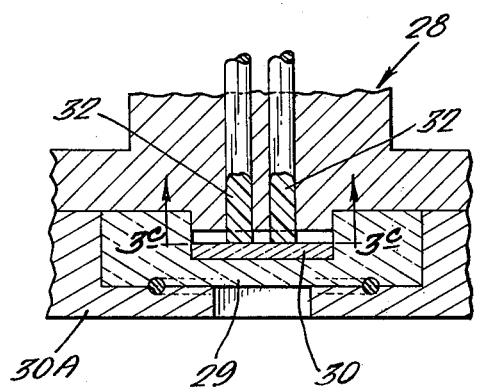
FIG. 3b is a fragmentary sectional view of the X-ray detector portion of the apparatus of FIG. 3, taken along lines 3b—3b.
Figure 3C:
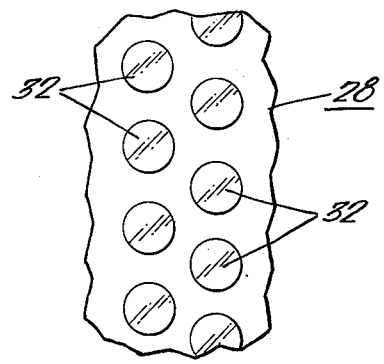
FIG. 3c is a fragmentary sectional view taken along lines 3c—3c of FIG. 3b.

The conveyor preferably moves the containers smoothly and continuously, and at a fixed predetermined speed, through the X-ray scanning station 14, which in this example comprises an X-ray source 26 positioned below the path of the containers, and having at its top an X-ray exit window 27 which extends across the full widths of the containers but is narrow in the direction of motion of the containers so as to transmit a beam of X-rays of generally rectangular cross section upward through the path traversed by the containers. Station 14 also comprises the X-ray detector system 28 positioned above and across the part of the containers and having its entrance window 29 in vertical alignment with the exit window 27 of the X-ray source. The X-ray detector system includes a phosphorescent strip of X-ray-responsive material 30 (see FIG. 3b) toward which the X-ray beam is directed, and a plurality N, e.g. 64, of light-conducting optical fibers such as 32, the lower ends of which are arranged in two rows along the length of the X-ray responsive strip as shown more clearly in FIG. 3c. More particularly, the lower ends of the optical fibers abut the upper surface of the X-ray responsive strip, and the two rows thereof are laterally displaced with respect to each other by one-half the spacing between them, so that the two sets together cover substantially completely the length of the phosphorescent strip beneath which the containers pass. A stainless steel tunnel 30A, 30B extends above and below the path of the containers at the X-ray station to provide protective shielding against stray X-rays.

Each of the light-conductive optical fibers such as 32 supplies light to a corresponding respective photomultiplier tube such as 34, when and only when the phosphorescent material directly under its lower end is impinged by X-rays. Thus N photomultipliers are employed, one such photomultiplier for each of the N light-conducting fibers; only one photomultiplier and subsequent corresponding electrical channel is shown, it being understood that (N-1) other identical photomultipliers and corresponding electrical channels are employed. Each of the photomultipliers produces a current in its output line 36 which decreases with decreases in the intensity of X-rays reaching the corresponding spot on the phosphorescent strip which is monitored by the above-mentioned lower end of that particular optical fiber. When bone is present in a portion of the meat aligned with the end of any particular optical fiber, the resultant "shadow" will normally decrease the output current of the photomultiplier associated with that fiber, and usually any such bones or bone fragments will in fact produce decreases in the output currents of the photomultipliers associated with other nearby fibers as well.

The N photomultipliers such as 34 are part of an electronic sensing and control unit 40 which responds to such decreases in photomultiplier output current due to the shadow of a bone to produce an output signal over line 42 to the reject mechanism 16 for operating the latter mechanism to its reject position when the container for which the bone shadow is detected reaches the reject mechanism; the reject mechanism tilts that container to dump the contents of any such container into any appropriate reject receptacle, thus preventing it from travelling through to the dumping and water removal station 18.

Each of the N channels in unit 40 comprises a thresholding circuit 41 which rejects all signal levels supplied thereto corresponding to detected X-ray intensities at least as great as that produced in the presence of bone, and passes substantially only signals representative of the presence of bone. Each of the latter signals comprise a relatively rapid change when the leading edge of the bone passes in front of that portion of the X-ray responsive strip 30 monitored by the corresponding optical fiber, and another oppositely directed change when the trailing edge of that bone traverse the latter position. This signal, produced only when bone is present, is in each case passed through a differentiator 43 which produces as its output line 44 a pulse signal of one polarity corresponding to the leading edge of the bone and a pulse signal of the opposite polarity corresponding to the trailing edge of the bone.

The latter differentiated signal is supplied to a unipolarizer circuit 46 to produce on its output line 48 pulses which are of the same polarity for the leading and trailing edges of the bone, rather than of opposite polarities. The latter pairs of pulses are passed through an OR gate 50 to a flip-flop curcuit 52, which flip-flop is actuated to a "set" condition whenever any one of the above-described pulses on line 48 exceeds a predetermined minimum amplitude.

OR gate 50 is also supplied with corresponding outputs from the N-1 other channels, so that a sufficient pulse produced by any of the other channels will also set the flop-flop 52. Accordingly, if as a food container passes through the X-ray station a bone or fragment of bone produces a substantial decrease in transmitted X-ray intensity, this will be detected by the above-described system as that bone passes beneath the X-ray responsive strip, and will set the flip-flop 52.

Since the reject mechanism 16 in this example is located somewhat downstream from the X-ray station, and there are other containers positioned between the X-ray station and the reject mechanism at the time of detection of bone in the container in the X-ray station, the actuation of flip-flop 52 is not utilized immediately to operate the reject mechanism, since this would reject a container ahead of the one intended to be rejected. Instead, the output of the flip-flop, occurring when it is set in response to detection of bone, is supplied over line 59 to a shift register 60, wherein it is stored and advanced from one internal register to the next each time a container passes the X-ray station, this advancing being repeated a number of times equal to the number of containers between the X-ray station and the reject mechanism, so that when the container in which bone is detected reaches the reject mechanism the reject mechanisms will operate at the proper time to reject that container. In the example shown the flip-flop output signal is stored in the register for three such periods before operating the reject mechanism. Rejection may be accomplished by automatic tilting of a container to dump its contents, by known techniques and apparatus.

The dumping and water removal station 18 for the meat which passes X-ray inspection may include a vibrating mesh 65 upon which the meat is dumped by automatic tilting of all containers, with the water running through the mesh and the meat moving along the vibrating mesh to its next desired position preparatory to its use in making chicken soup.

In order to synchronize the resetting of the flip-flop 52 prior to the entrance of each container into the X-ray station, as well as to synchronize the shifting operations of the shift register 60, a conveyor position monitor 66 is employed, which may take any of a variety of forms for sensing when each container reaches a certain position, and in this case (see FIGS. 5 and 5a) may take the form of a toothed wheel 68, having teeth engaging with the links of a drive chain 69 of the conveyor 10 so as to turn with motion of the chain, and having a number of teeth such that it executes one complete rotation when the chain moves by a distance equal to the distance between the leading edges of successive containers. A sleeve 70 mounted to turn with wheel 68 is provided with a narrow slit 72, a source of light 74 within the sleeve, and a photoelectric detector 76 outside the sleeve; thus each time the wheel 68 executes one complete revolution, the photocell 76 will produce an output current on its output lead 80 to reset the flip-flop and to shift any signal stored in the shift register by one stage. Set screws 82 may be provided to permit initial setting of the sleeve 70 to any desired angular position with respect to the wheel 68, so as to cause the output current on line 80 to occur for any desired position of the container. In the present example, this adjustment is preferably such that a pulse current on output line 80 occurs when each container has just left the X-ray station. The occurrence of the current in line 80 then acts through a clock and reset circuit 90 to produce at that time a flip-flop reset signal over line 92 for resetting the flip-flop, and a clock signal over line 94 to shift register 60 to advance any bone-representing signal stored therein to the next register stage or to the reject mechanism from the last stage of the shift register.

Referring now to FIG. 4A, in which ordinates of the full-line graph represent current from one of the photomultipliers and abscissae represent time, the current level $a$ represents the high level of current existing when no container intervenes between the X-ray source and the X-ray detector system, the somewhat lower level $b$ represents the photomultiplier output curent when the transmitted X-ray intensity has been reduced somewhat by passing through the end wall of the container, and the much lower level $c$ represents the photomultiplier output current when a container has moved into the X-ray station to a position such that the X-rays are transmitted through the combination of chicken meat and water without traversing bone or bubbles. At $d$ the current has fallen even closer to zero momentarily, because a bone has intervened between the X-ray source and the lower end of the particular optical fiber delivering light to the photomultiplier tube here being considered. At $e$, the current has returned to the same level as at $c$ indicating that bone is no longer in line with the particular optical fiber in question. The level at $f$ represents the increased photomultiplier current produced upon the occurrence of a void or bubble within the water, which does not absorb X-rays as readily as the water or the meat and thus provides a momentary increase in photomultiplier output current. At $g$ there is represented a return to the level characteristic of the combination of meat and water without bubbles or voids. The subsequent levels $h$ and $i$ correspond substantially exactly to the levels $b$ and $a$ respectively, and are produced at and beyond the trailing edge of the container being considered.

The thresholding circuit 41, to which a signal like that shown in FIG. 4A is applied, operates in effect to remove all levels of the applied signal at least as great as the level $c,e,g$ produced when only meat and water are being scanned by the X-rays, thereby leaving only the pulse corresponding to the decreased X-ray intensity caused by the shadow of bone, as represented in FIG. 4B. It is noted that, by this thresholding, not only are the signal levels occurring between containers and during scanning of container walls eliminated, but the randomly-occurring photomultiplier output signals due to voids or bubbles are also eliminated, thereby avoiding certain problems to be discussed in more detail hereinafter.

When the signal represented in FIG. 4B has passed through the differentiator 42, the resultant differentiated signal is as represented in FIG. 4C, consisting of an earlier negative-going differentiated pulse corresponding to the leading edge of the bone and a following positive-going pulse corresponding to the trailing edge of the bone.

FIG. 4D represents the output of the unipolarizer circuit 46, comprising a positive pulse corresponding to the negative pulse of FIG. 4C and a positive pulse corresponding to the positive pulse of FIG. 4C. These two positive-going pulses are applied to the flip-flop 52; in this example, the first of these pulses is sufficient to actuate the flip-flop and initiate operation of the reject mechanism as desired, although if only the second of this pair of pulses is sufficient to activate the flip-flop it will do so.

Referring back again to FIG. 4A, there is shown in broken line a waveform which might typically be produced by a photomultiplier at the X-ray station if no water had been added to the containers. In this case there is no void or bubble problem per se, since liquid is not present. However, due to the random irregularities of the vertical thicknesses in the chicken meat specimen, the output of the photomultiplier varies very substantially even in the absence of bone, so that the decrease in current due to the bone is not readily distinguishable from other random variations existing in the photomultiplier output signal, and in some cases may in fact consititute a much smaller variation than the random variations. Thus if the threshold level in the electronic circuitry were set high enough to prevent operation on such random variations, the bone would not be able to produce the desired actuation, while if the level were set sufficiently low to permit bone-generated signals to actuate the reject mechanism, the other random variations present would also have this same effect even though no bone was present. The result is that such an arrangement can provide even reasonable reliability only for very thick, dense, bones which will absorb the X-rays so strongly that the resultant change in photomultiplier output signal can easily be distinguished from other random variations therein. However, such an arrangement would not permit the reliable and sensitive detection of smaller or less absorptive bone or one fragments, an operation which can however be obtained by the above-described filling of the container to a fixed reference level. It is also noted that since this fixed reference level of filling is the same for all containers, the threshold level suitable for use in connection with the detection of bone in one container is also suitable for use in connection with all the containers, and an accurate automatic system suitable for use with successive containers on a conveyor is thereby made possible.

The significance of utilizing the thresholding operation ahead of the differentiating operation may now also be appreciated. Thus it will be seen that if the signal shown in full line in FIG. 4A were differentiated directly, not only would the desired negative and positive pulses be generated by the bone-representing signal, but there would also be positive and negative differentiated pulses produced by any void which might be present. The pulses produced by the void can be such as to cause actuation of the reject mechanism even if the bone-representing signals are not present, thus improperly causing rejection of chicken meat without chicken bones in it. This is prevented by thresholding the signal prior to differentiation to eliminate signals due to voids.

The significance of the unipolarizer circuit operation will also now be appreciated. Thus when attempting to detect the smallest and/or most porous types of bone, operation is near the margin of the capability of the system. The unipolarizer permits response both to signals generated by the leading edges and signals generated by the trailing edges of the bone. In the first place, this provides two opportunities for the system to be actuated, instead of one, so that if noise or other variations should prevent one of these two pulses from actuating the reject mechanism, the other pulse may be successful in doing so. Also, it is quite possible that the gradient of X-ray absorption adjacent one edge may be more gradual than at the other edge, resulting in a larger differentiated pulse for one edge than for the other, and with the arrangement of the invention in its preferred form it is assured that the greater of the two differentiated pulses will be given an opportunity to operate the flip-flop and reject mechanism.

FIG. 6 illustrates one particularly advantageous specific circuit arrangement for one of the N channels in the electronic sensing and control circuit 40, from the photomultiplier 34 to the OR gate 50. The photomultiplier tube 34 is shown supplied at its cathode with a highly negative potential by means of voltage source 100, the positive terminal of which source is connected to ground as shown. The latter source is usually a very high voltage, for example making the photomultiplier cathode of the order of 1,000 volts negative with respect to ground. The supply circuits for the several dynodes in the photomultiplier are not shown, since they are conventional. The photomultiplier has the known effect of producing at its anode a current many times greater than that produced at its cathode by light impingent thereon. The anode of the photomultiplier is connected to the anode of a diode rectifier 102 in the thresholding circuit 41, the cathode of which diode is returned to ground through the resistors in the adjustable cathode-biasing circuit 104.

The diode 102 conducts and passes signal variations only when its anode is somewhat positive with respect to its cathode; the cathode biasing circuit 104 permits this conduction point of the diode 102 to occur at rectifier anode voltages as close to ground as desired. In this preferred example, the thresholding circuit includes a special stable current-biasing circuit 106, but the operation may best be understood by first considering a simpler form of this circuit in which the anode of diode 102 is assumed merely to be connected to a manually-adjustable positive voltage source by way of a resistor. With such a simplified circuit, part of the current from the manually-adjustable source will flow to the anode of the photomultiplier tube 34, and the remainder to the anode of the diode rectifier 102 and through the cathode circuit of the rectifier, so long as the diode rectifier is conducting. When the photomultiplier cathode is completely dark, all of the current from the manually-adjustable source will flow through the rectifier 102; however, as the cathode of the photomultiplier tube is subjected to increasing illumination, progressively more of this current will be diverted from the anode of rectifier 102 to the anode of the photomultiplier tube, and the current through the cathode circuit of the rectifier will therefore decrease, since it equals the difference between the current at the voltage source and the current to the photomultiplier anode.

At a certain level of illumination of the photomultiplier cathode determined by the adjustment of the manually-adjustable voltage source, substantially all of this current will be diverted through the photomultiplier tube, the rectifier 102 will no longer conduct, and in fact there will be no appreciable current in the cathode circuit of rectifier 102 whenever the illumination of the photomultiplier is above this level. Adjustment of the manually-adjustable voltage source therefore adjusts this illumination level above which cathode current is no longer produced in the cathode circuit of the rectifier 102; below this level, variations in the illumination will produce corresponding variations in the cathode current of rectifier 102. Accordingly, it is possible to set the level of the manually-adjustable voltage source to prevent variations in cathode current of rectifier 102 whenever the X-ray intensity causing illumination of the photomultiplier tube is above a reference level produced by chicken meat and water, but no bone or other foreign material, in the container being X-rayed. Because of unavoidable electrical noise in the photomultiplier output signal, the threshold level thus established by the manually-adjustable voltage source is preferably adjusted sufficiently to prevent peaks of noise from causing substantial cathode current from the rectifier 102, and since each photomultiplier channel is typically slightly different electrically, individual adjustments of such manually-adjustable voltage would be made in each channel to set the individual threshold levels as desired.

It has been found that the optimum threshold level is often quite sensitive to short-term variations due to such factors as unavoidable temperature changes, requiring in some cases rather frequent individual readjustment of the threshold controls for each of a relatively large number of channels and photomultipliers. Accordingly, in the preferred circuit of FIG. 6 an adjustable voltage source provided by the variable tap 108 on the resistor 109 connected between positive and negative supply voltage points, is connected to the negative input terminal of an operational amplifier device 110, the non-inverting input terminal of which is grounded and the output of which is supplied through a series resistor 114 to the anode of diode rectifier 102; a feedback resistor 116 is connected between the anode of diode rectifier 102 and the inverting terminal of the operational amplifier. A relatively large-valued capacitor 117 is also connected directly between the output terminal and the inverting input terminal of the amplifier device 110. The current supplied through resistor 114 then operates to produce thresholding in the same manner as the current from the above-described manual thresholding circuit, the level of thresholding being initially set as desired by the adjustment of the tap 108; however, because of the capacitor 117 connected in the circuit of the operational amplifier device 106, this circuit acts as an integrator, the time constant of which may be typically selected to provide an output-current averaging effect over a time period of, for example, the interval required for the passage of ten or twenty meat containers through the X-ray station. The effect of this is to substantially eliminate ordinary unavoidable short-term fluctuations in thresholding current, thus avoiding the need for frequent readjustment of the thresholding circuits in each of the N channels in order to produce the greatest reliable sensitivity of the system.

The cathode of the diode rectifier 102 is also connected through the capacitor 119 to the inverting input terminal of operational amplifier circuit 120; capacitor 119, in connection with the resistance in the cathode circuit 104 of rectifier 102, provides the desired differentiating function for the bone-representing signals. Amplifier 120 may take any of a variety of conventional forms, such as the Philbrick type 142802 amplifier.

The output of amplifier 120 is connected to the unipolarizer circuit 46, which as shown as a known conventional type of circuit identified as the Motorola Dual Op-amp Type MC 1747CL. The nature and operation of such circuits being well known in the art, it will not be necessary to describe them herein in detail. In general, the function of this circuit is to select a differentiated pulse of one polarity, amplify it, and pass it through the circuit to its output terminal in its original polarity; and to select the differentiated pulse of the other polarity, amplify it, and supply it to the same output terminal in its inverted polarity, so that the oppositely-directed differentiated pulses at the input of the circuit appear as pulses of the same polarity at the output terminal.

In a preferred embodiment of the invention, the latter unipolarized pairs of differentiated pulses are supplied to a single-shot pulse stretcher 130 to increase the time duration of each pulse for convenience in operating a light-emitting diode indicator 132, which may also be of conventional form and merely serves to produce a visible light indication persisting for a few seconds whenever an output pulse from circuit 46 indicates that bone has been detected. The output of circuit 46 may also be supplied through an inverter 140 to an isolating diode 142 providing, in connection with similar isolating diodes for each of the N other channels, the desired OR function. The common output from this set of diodes is supplied to the flip-flop 52, so that the flip-flop is actuated by any bone-representing pulse from any of the N channels as described above.

The X-rays need not be directed from bottom to top of the container, but may travel in the opposite direction or in other directions such as from one side to the other of the container, using an x-ray exit window and detector extending parallel to the height of the container; however, in any case the total thickness of meat and water is preferably uniform along the path of the X-rays. It is also possible to use signals from both edges of the bone without employing a unipolarizer, for example by utilizing conventional circuitry which will sense signal departures in either sense. A flowable material other than water can also be used, provided its X-ray absorption coefficient is sufficiently close to that of the food substance.

Any of many forms of mechanical apparatus may be used to provide the motion of the containers along a conveyor, the dumping of selected containers by the reject mechanism, and the subsequent dumping of all containers. In the example shown, and made especially clear in FIGS. 2, 2a and 3, each container may be pivotably supported on one side by the moving chain 69 and on the other side by the moving chain 69A, by means of respective inwardly-extending stub shafts 200, 202 mounted on links of the chain and inserted into respective centrally-bored bosses 204, 206 integral with opposite sides of the container. The chains 69, 69A are supported by, and ride on, the respective side rails 210, 212, and where the container is intended to ride level it is guided by a guide rail 214 on which ride the pair of longitudinally-spaced-apart rollers 220, 222 extending outward from the corresponding side of the container. Where the container is to be dumped by tilting it forwardly, the guide rail is eliminated to permit the container to pivot, and a camming ramp is placed in position to contact the cam-following boss 230 on the opposite side of the container. At the final dumping and water renewal station 18, the latter arrangement is permanently present; at the reject mechanism the guide rail is lowered and the camming ramp moved upwardly into operative position only when rejection is to be accomplished, for example by a pneumatic cylinder actuated by an electrical solenoid in response to a reject signal on line 42. Suitable details of such mechanisms for accomplishing the desired automatic dumping will be obvious to one skilled in the art.

While the invention has been described with particular reference to specific embodiments in the interest of complete definiteness, it will be understood that it may be embodied in a variety of forms diverse from those specifically shown and described, without departing from the spirit and scope of the invention as defined by the appended claims.

What is claimed is:

1. In a method for automatically detecting bone in meat by passing successive specimens of said meat through an X-ray detection station and detecting decreases in transmitted X-ray intensity due to the presence of bone in any of said specimens:

placing each of said successive meat specimens in a corresponding container together with sufficient water to provide the same thickness, in each container, for the combination of water and meat along a given direction in said each container; successively passing each of said containers with its meat specimen and water through said X-ray detection station so that said X-rays are transmitted therethrough along said given direction; deriving at said X-ray station electrical signals representative of the intensities of said transmitted X-rays as each of said container moves through said X-rays; passing said electrical signals through a threshold device to eliminate levels of said electrical signals greater than a reference level thereof produced in the absence of bone in said meat; and sensing changes in said electrical signals from said threshold device to produce signal pulses in response to an edge of bone present in said meat.

2. The method of claim 1, comprising producing said signal pulses in responses to both edges of said bone, and producing bone-representing indications in response to said pulse signals due to either the leading edge or the trailing edge of said bone.

3. The method of claim 1, in which said signal pulses produced by said leading and trailing bone edges extend in opposite senses, said method also comprising modifying said pulses to extend in the same direction, and producing bone-representing indications only when at least one of said modified pulses exceeds a predetermined value.

4. A system for detecting the presence of foreign material in a food substance, comprising:

a container for said food substances;
   means for filling said container to above the top of said food sustance with a flowable substance having an X-ray absorption coefficient close to that of said food substance;

an X-ray station comprising a source of X-rays and a detector of said X-rays spaced from said source for developing electrical signals representative of the intensities of X-rays reaching it from said source;

means for moving said container, with said food substance and said flowable substance in it, through the space between said X-ray source and said X-ray detector thereby to produce identifiable changes in said electrical signals as said X-rays scan said foreign material;

threshold means for eliminating from said electrical signals levels thereof corresponding to intensities of said detected X-rays at least as great as those produced in the absence of said foreign material.

5. A system for detecting the presence of foreign material in a food substance, comprising:

a container for said food substance;

means for filling said container to above the top of said food substance with a flowable substance having an X-ray absorption coefficient close to that of said food substance;

an X-ray station comprising a source of X-rays and a detector of said X-rays spaced from said source for developing electrical signals representative of the intensities of X-rays reaching it from said source;

means for moving said container, with said food substance and said flowable substance in it, through the space between said X-ray source and said X-ray detector thereby to produce identifiable changes in said electrical signals as said X-rays scan said foreign material;

means for differentiating said signals to produce electrical pulses in response to both the leading and trailing edges of said foreign material;

threshold means for eliminating from said electrical signals, prior to their application to said differentiating means, levels thereof corresponding to detected X-ray intensities at least as great as those produced in the absence of said foreign material.

6. The system of claim 5, comprising unipolarizing means for producing, from said differentiated signals, pulse signals of the same polarity in response to both said leading and trailing edges of said foreign material, and means for producing indications of the occurrence of at least one of said unipolarized pulse signals.

7. The method of automatically detecting the presence of bone in meat, comprising:

placing said meat in an X-ray pervious container;

filling said container to a level above the top of said meat with a liquid having a coefficient of X-ray absorption near that of said meat;

passing said container with said meat and liquid therein between an X-ray source and an X-ray detector to scan said meat and liquid with X-rays, and to produce electrical signals representing the degree of absorption of said X-rays by successive portions of said meat and liquid combination, whereby bone present in said container causes a reduction in intensity of detected X-rays from a reference level to a bone-representing level and also produces levels of said electrical signals departing from reference levels thereof produced when bone is absent;

eliminating levels of said electrical signals corresponding to levels of said detected X-rays at least as great as said reference level of X-rays, while retaining those of said electrical signals corresponding to said bone-representing X-ray levels;

differentiating said retained electrical signals to produce a signal pulse of a first polarity at the leading edge and another signal pulse of the opposite polarity at the trailing edge of each bone;

modifying said differentiated electrical signals so that said pulses are all of the same polarity;

producing a bone-representing indication in response to said modified differentiated electrical signals; and separating said meat from said liquid after said scanning by said X-rays.

8. The method of claim 7, in which said liquid is water.

9. In a method for automatically detecting foreign material in a food substance by the transmission through said food substances of radiations for which said foreign material has a greater coefficient of absorption than does said food substance, said method comprising placing about said food substance a flowable material having substantially the same value of said coefficient as said food substance to form substantially parallel opposite surfaces for the combination of said food substance and said flowable material, scanning said food substance with said radiations while transmitting said radiations through both of said parallel surfaces, sensing changes in the strength of said transmitted radiations to produce electrical signals representative of the strenths of said transmitted radiations, and differentiating said electrical signals to produce differentiated signals representative of scanning of said radiations across edges of said foreign material, the improvement comprising:

prior to said differentiating, eliminating levels of said electrical signals corresponding to strengths of said transmitted radiations at least as great as those produced when scanning regions containing only said food substance and said flowable material, whereby interfering differentiated signals due to scanning of voids or bubbles in the scanned material are eliminated while differentiated signals due to said foreign material are retained.

10. The method of claim 9, in which said flowable material is a liquid.

11. The method of claim 10, in which said liquid is water.

* * * * *